United States Patent
George et al.

(10) Patent No.: US 7,918,782 B2
(45) Date of Patent: Apr. 5, 2011

(54) PROSTHESIS WITH BLADDER THAT ADJUSTS GIRTH

(75) Inventors: Stephanie A. George, St. Louis Park, MN (US); Sara Elizabeth Nelson, Plymouth, MN (US); Randall P. Rowland, Eden Prairie, MN (US); Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/272,080

(22) Filed: Nov. 17, 2008

(65) Prior Publication Data
US 2009/0132043 A1    May 21, 2009

Related U.S. Application Data

(60) Provisional application No. 60/988,264, filed on Nov. 15, 2007.

(51) Int. Cl.
*A61F 13/00* (2006.01)
(52) U.S. Cl. ......................................................... 600/40
(58) Field of Classification Search .............. 600/38–41; 128/897–898
See application file for complete search history.

(56) References Cited

U.S. PATENT DOCUMENTS

| | | | |
|---|---|---|---|
| 525,020 A | 8/1894 | Jungner | |
| 734,498 A * | 7/1903 | Bachler | 606/192 |
| 2,455,859 A | 12/1948 | Foley | |
| 2,533,924 A | 12/1950 | Foley | |
| 3,538,917 A | 11/1970 | Selker | |
| 3,642,005 A | 2/1972 | McGinnis | |
| 3,720,200 A | 3/1973 | Laird | |
| 3,744,063 A | 7/1973 | McWhorter et al. | |
| 3,750,194 A | 8/1973 | Summers | |
| 3,853,122 A | 12/1974 | Strauch et al. | |
| 3,863,622 A | 2/1975 | Buuck | |
| 4,201,202 A * | 5/1980 | Finney et al. | 600/40 |
| 4,222,377 A | 9/1980 | Burton | |
| 4,224,370 A | 9/1980 | Heinemann | |
| 4,267,829 A * | 5/1981 | Burton et al. | 600/40 |
| 4,342,308 A | 8/1982 | Trick | |
| 4,353,360 A * | 10/1982 | Finney et al. | 600/40 |
| 4,360,010 A * | 11/1982 | Finney | 600/40 |
| RE31,121 E | 1/1983 | Reinicke | |
| 4,383,525 A * | 5/1983 | Scott et al. | 600/40 |
| 4,386,601 A | 6/1983 | Trick | |
| 4,408,597 A | 10/1983 | Tenney, Jr. | |
| 4,412,530 A | 11/1983 | Burton | |
| 4,417,567 A | 11/1983 | Trick | |
| 4,419,985 A | 12/1983 | Trick | |

(Continued)

OTHER PUBLICATIONS

U.S. Appl. No. 61/140,173, filed Dec. 23, 2008.

(Continued)

*Primary Examiner* — Samuel G Gilbert
(74) *Attorney, Agent, or Firm* — Kimberly K. Baxter; Gregory L. Koeller

(57) ABSTRACT

A prosthetic device comprises a column formed of resilient material and having a proximal end and a distal end. The prosthetic device comprises a bladder having a liquid cavity at the distal end. The bladder is inflatable and deflatable to increase and decrease a girth at the distal end of the prosthetic device. The prosthetic device comprises a liquid supply system that couples along the column to the bladder for selectively controlling liquid flow to the bladder to increase and decrease the girth.

18 Claims, 4 Drawing Sheets

U.S. PATENT DOCUMENTS

| | | | |
|---|---|---|---|
| 4,502,159 A | 3/1985 | Woodroof et al. | |
| 4,523,584 A * | 6/1985 | Yachia et al. | 600/38 |
| 4,549,531 A | 10/1985 | Trick | |
| 4,550,720 A | 11/1985 | Trick | |
| 4,553,533 A | 11/1985 | Leighton | |
| 4,558,693 A * | 12/1985 | Lash et al. | 600/40 |
| 4,566,446 A | 1/1986 | Fogarty | |
| 4,584,990 A | 4/1986 | Haber et al. | |
| 4,634,443 A | 1/1987 | Haber | |
| 4,682,583 A | 7/1987 | Burton et al. | |
| 4,708,140 A | 11/1987 | Baron | |
| 4,829,990 A | 5/1989 | Thuroff et al. | |
| 4,834,115 A | 5/1989 | Stewart | |
| 4,878,889 A | 11/1989 | Polyak | |
| 4,969,474 A | 11/1990 | Schwarz | |
| 4,994,020 A | 2/1991 | Polyak | |
| 5,012,822 A | 5/1991 | Schwarz | |
| 5,050,592 A * | 9/1991 | Olmedo | 600/40 |
| 5,078,676 A | 1/1992 | Bailly | |
| 5,088,980 A | 2/1992 | Leighton | |
| 5,097,848 A | 3/1992 | Schwarz | |
| 5,370,690 A | 12/1994 | Barrett | |
| 5,562,598 A | 10/1996 | Whalen et al. | |
| 5,570,690 A | 11/1996 | Yoon | |
| 5,634,878 A | 6/1997 | Grundei et al. | |
| 5,782,916 A | 7/1998 | Pintauro et al. | |
| 5,851,176 A | 12/1998 | Willard | |
| 5,893,826 A | 4/1999 | Salama | |
| 5,989,288 A | 11/1999 | Pintauro et al. | |
| 6,013,102 A | 1/2000 | Pintauro et al. | |
| 6,063,119 A | 5/2000 | Pintauro et al. | |
| 6,095,969 A | 8/2000 | Karram et al. | |
| 6,171,233 B1 | 1/2001 | Willard | |
| 6,183,520 B1 | 2/2001 | Pintauro et al. | |
| 6,328,687 B1 | 12/2001 | Karram et al. | |
| 6,354,991 B1 | 3/2002 | Gross et al. | |
| 6,432,038 B1 | 8/2002 | Bakane | |
| 6,432,040 B1 | 8/2002 | Meah | |
| 6,443,887 B1 | 9/2002 | Derus et al. | |
| 6,464,999 B1 | 10/2002 | Huo et al. | |
| 6,533,719 B2 | 3/2003 | Kuyava et al. | |
| 6,652,449 B1 | 11/2003 | Gross et al. | |
| 6,659,937 B2 | 12/2003 | Polsky et al. | |
| 6,689,046 B2 | 2/2004 | Sayet et al. | |
| 6,712,772 B2 | 3/2004 | Cohen et al. | |
| 6,723,042 B2 | 4/2004 | Almli et al. | |
| 6,730,017 B2 | 5/2004 | Henkel et al. | |
| 6,749,556 B2 | 6/2004 | Banik | |
| 6,862,480 B2 | 3/2005 | Cohen et al. | |
| 6,896,651 B2 | 5/2005 | Gross et al. | |
| 6,915,165 B2 | 7/2005 | Forsell | |
| 6,921,360 B2 | 7/2005 | Banik | |
| 6,935,847 B2 | 8/2005 | Kuyava et al. | |
| 6,991,601 B2 | 1/2006 | Kuyava et al. | |
| 7,128,707 B2 | 10/2006 | Banik | |
| 7,169,103 B2 | 1/2007 | Ling et al. | |
| 7,244,227 B2 | 7/2007 | Morningstar | |
| 7,250,026 B2 | 7/2007 | Kuyava | |
| 7,350,538 B2 | 4/2008 | Kuyava et al. | |
| 7,387,603 B2 | 6/2008 | Gross et al. | |
| 7,400,926 B2 | 7/2008 | Forsell | |
| 7,407,482 B2 | 8/2008 | Kuyava | |
| 2004/0167574 A1 | 8/2004 | Kuyava et al. | |
| 2005/0075534 A1 | 4/2005 | Kuyava | |

OTHER PUBLICATIONS

U.S. Appl. No. 61/140,350, filed Dec. 23, 2008.
American Medical Systems, DURA II Positionable Penile Prosthesis 12 Step Procedure Guide, 2003, pp. 1-6, American Medical Systems, Inc., USA.
U.S. Appl. No. 12/644,805, filed Dec. 22, 2009.
U.S. Appl. No. 60/988,264, filed Nov. 15, 2007.

* cited by examiner

PROSTHESIS WITH BLADDER THAT ADJUSTS GIRTH

CLAIM TO PRIORITY

The present application claim priority to U.S. Provisional Patent Application No. 60/988,264, filed Nov. 15, 2007, and entitled "Prosthesis with Bladder that Adjust Girth". The identified provisional patent application is hereby incorporated by reference in its entirety.

FIELD OF THE INVENTION

The present invention relates to implantable prostheses. In particular, but not by way of limitation, the present invention relates to implantable malleable (non-inflatable) penile prostheses.

SUMMARY OF THE INVENTION

Disclosed is a prosthetic device. The prosthetic device comprises a column formed of resilient material and having a proximal end and a distal end. The prosthetic device comprises a bladder having a liquid cavity at the distal end. The bladder is inflatable and deflatable to increase and decrease a girth at the distal end of the prosthetic device. The prosthetic device comprises a liquid supply system that couples along the column to the bladder for selectively controlling liquid flow to the bladder to increase and decrease the girth.

DETAILED DESCRIPTION OF ILLUSTRATIVE EMBODIMENTS

In the embodiments described below, an implantable penile prosthesis includes a bladder at a distal end of the prosthesis. The bladder is inflatable and deflatable to change the girth of the prosthesis. A liquid supply system selectively controls flow of fluid to the bladder. The liquid supply system is manually actuatable by the patient.

Figure 1:
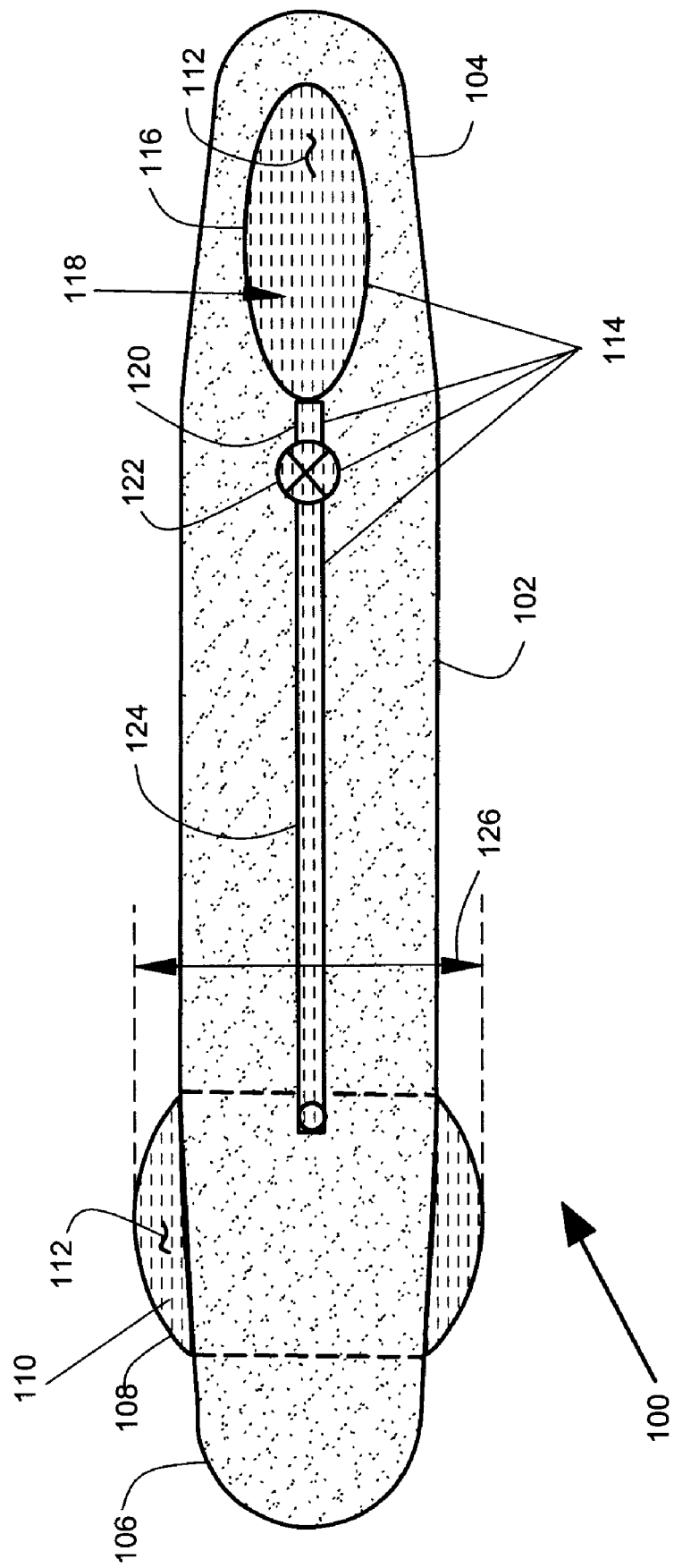
FIG. 1 illustrates a first embodiment of a prosthetic device.

FIG. 1 illustrates a prosthetic device 100. The prosthetic device 100 comprises a column 102 formed of resilient material. The column 102 extends from a proximal end 104 to a distal end 106.

The prosthetic device 100 comprises a bladder 108. The bladder 108 has a generally toroidal shape and is positioned and attached around an external surface to the column 102 adjacent the distal end 106. The bladder 108 surrounds a liquid cavity 110. The bladder 108 is inflatable by filling the liquid cavity 110 with a liquid 112 as illustrated. The bladder 108 is deflatable by draining the liquid 112 from the liquid cavity 110 of the bladder 108. In one embodiment, the liquid 112 comprises silicone oil. In another embodiment, the liquid 112 comprises a saline solution.

The bladder 108 is fluidly coupled to a liquid supply system 114. The liquid supply system 114 supplies liquid 112 for inflating the bladder 108, and receives liquid 112 when the bladder is deflated.

A liquid supply system 114 couples to the proximal end to receive a force for selectively pumping liquid 112 to the bladder 108. The liquid supply system 114 comprises a collapsible reservoir 116 that has a reservoir cavity 118 for holding the fluid 112. The collapsible reservoir 116 is collapsible by manually squeezing the proximal end 104 of the column 102. As the collapsible reservoir 116 collapses due to externally applied force, liquid 112 is forced out of the reservoir cavity 118 and flows through a passageway 120, a valve 122 and a passageway 124 to the liquid cavity 110, inflating the bladder 108. Inflating the bladder 108 increase girth 126 at the distal end 106. Alternatively, an external mechanical pressure or force is applied to the bladder 108, pumping liquid 112 from the bladder 108 to the reservoir cavity 118 to reduce the girth 126. The valve 122 controls the flow of liquid 112. The bladder 108 is described in more detail below by way of an example illustrated in FIG. 3. The valve 122 is described in more detail below by way of an example illustrated in FIG. 4.

Figure 2:
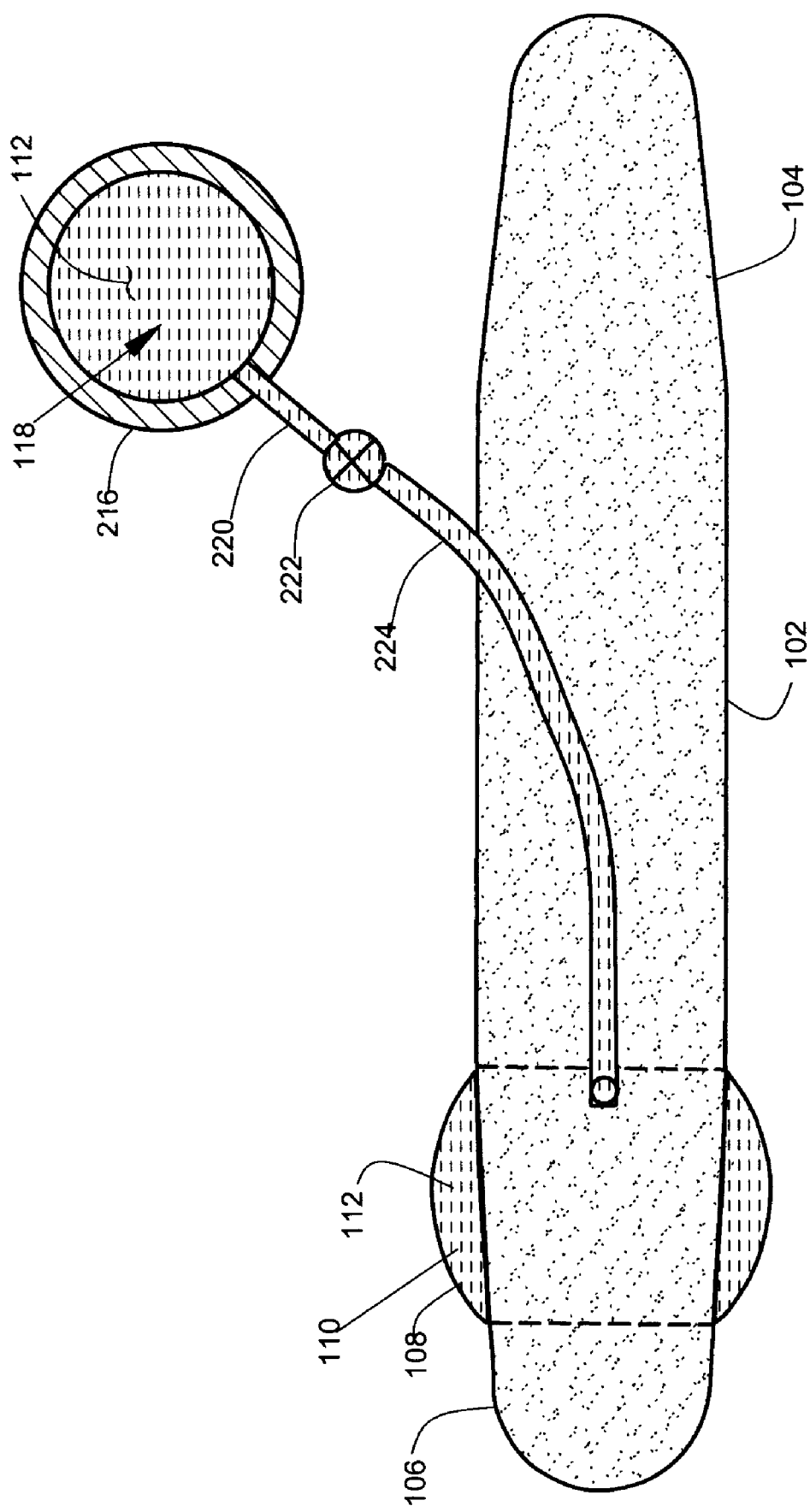
FIG. 2 illustrates a second embodiment of a prosthetic device.

FIG. 2 illustrates a prosthetic device 200. The prosthetic device 200 is similar to the prosthetic device 100 except that the prosthetic device 200 has a collapsible reservoir 216, passageway 220 and valve 222 that are located external to a column 102 as illustrated. A passageway 224 extends from the external valve 222 to the bladder 108. In other respects, the prosthetic device 200 and the prosthetic device 100 are similar. Reference numbers shown in FIG. 2 that are the same as reference number shown in FIG. 1 identify similar features.

Figure 3:
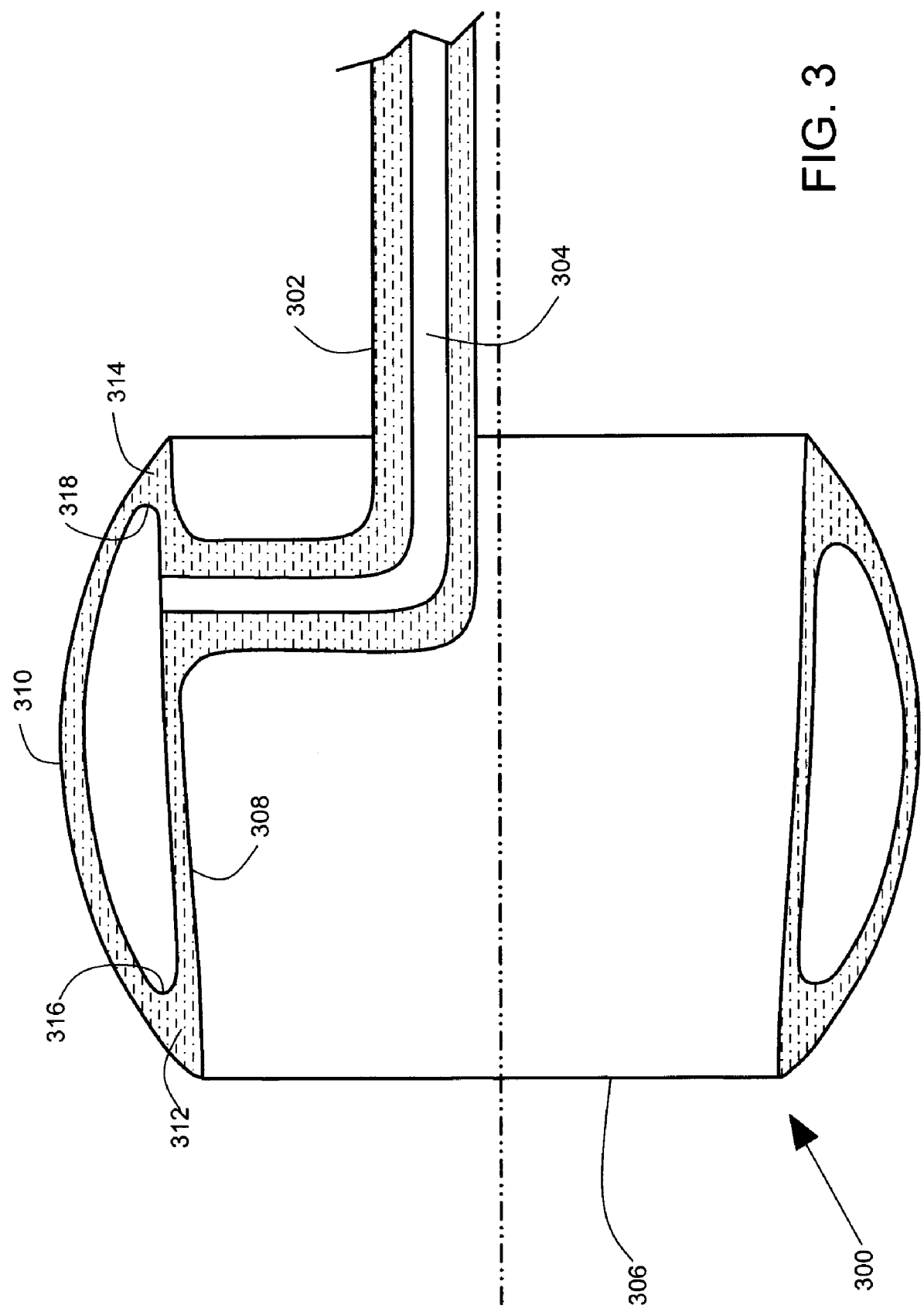
FIG. 3 illustrates an embodiment of a bladder that changes girth.

FIG. 3 illustrates an exemplary bladder 300 that can be used in the embodiments 100, 200 illustrated in FIGS. 1-2. In one embodiment, the bladder 300 comprises silicone rubber. In another embodiment, the bladder 300 comprise thermoplastic resin. The bladder 300 comprises an inlet/outlet tube 302. In one embodiment, the inlet/outlet tube 302 connects to a passageway such as passageway 124 in FIG. 1. In another embodiment, the inlet/outlet tube 302 is the passageway 124 in FIG. 1. In one embodiment, a wall thickness of the inlet/outlet tube 302 is sufficient to contain internal fluid pressure without significantly inflating the inlet/outlet tube 302. In yet another embodiment, the inlet/outlet tube 302 is embedded in a column 102 such that the column 102 restrains any significant inflation of the inlet/outlet tube 302.

The bladder 300 comprises a main bladder body 306 that has a generally round cylindrical shape as illustrated. The main bladder body 306 comprises a bladder body inner wall 308. The inner wall 308 is supported on a central column that prevents any significant inflation of the inner wall 308. The main bladder body 306 comprises an outer wall 310. The outer wall 310 is inflatable by pressurized fluid in the main bladder body 306. The outer wall 310 and the inner wall 308 are joined along circular joining regions 312, 314. In one embodiment, the circular joining regions 312, 314 comprise non-sharp, rounded inner corner surfaces 316, 318. The joining regions 312, 314 are in tension when the bladder 300 is inflated. The rounding of the inner corner surfaces 316, 318 prevents stress concentrations at the inner corner surfaces and reduces risk of cracking the joining regions 312, 314. In one embodiment, the bladder 300 is a unitary body, completely free of joints, and is a single casting. In one exemplary process, the bladder 300 is rotationally cast to distribute resin on die surfaces. In another exemplary process, the bladder 300 is cast using a meltable or dissolvable casting insert to define hollow regions of the bladder 300, and the casting insert is later melted or dissolved to remove the insert. Other known methods of casting complex shapes in resilient materials can also be used.

Figure 4:
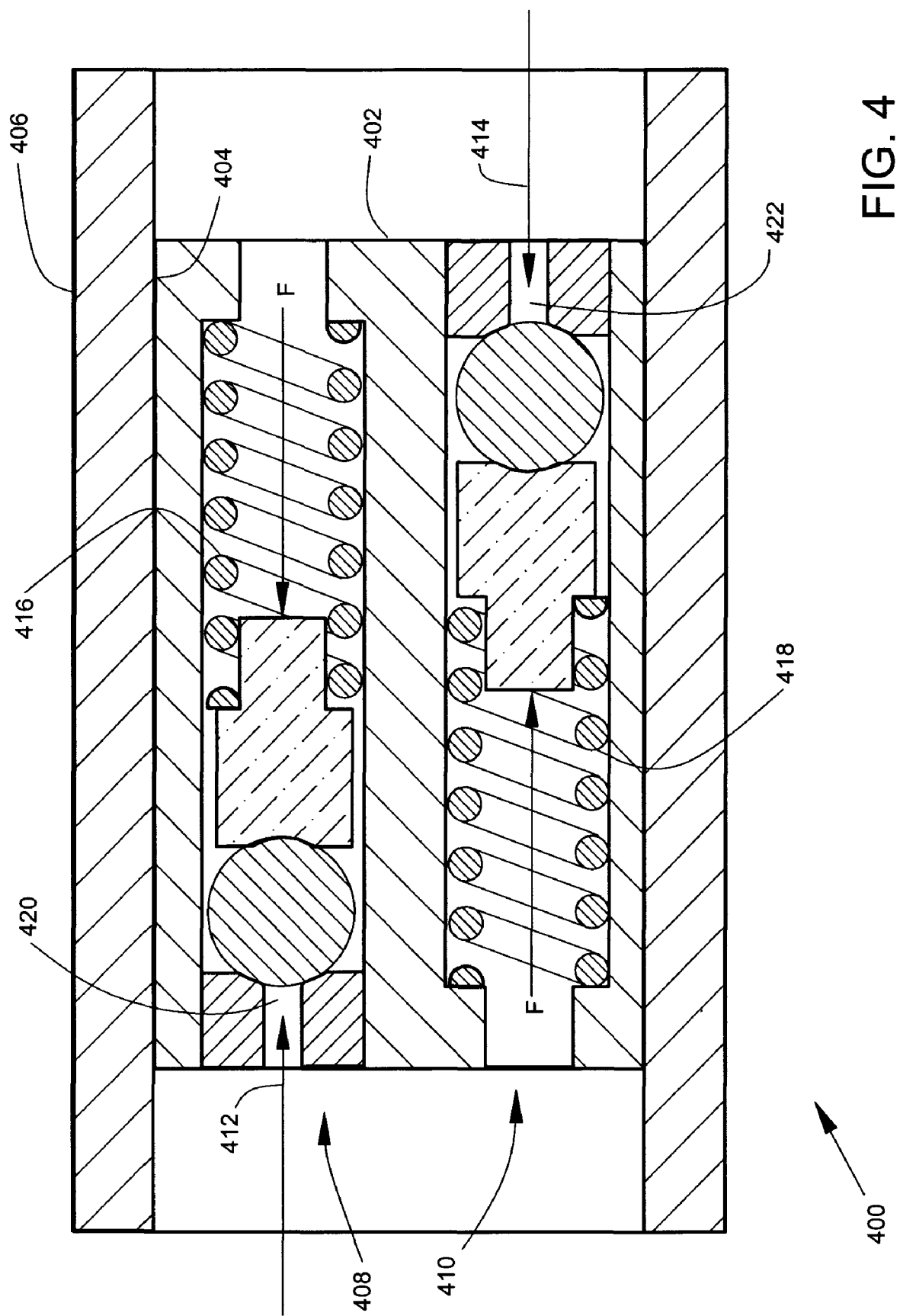
FIG. 4 illustrates an embodiment of a valve.

FIG. 4 illustrates an exemplary valve 400 that can be used in the embodiments 100, 200 illustrated in FIGS. 1-2. The valve 400 includes a valve body 402. The valve body 402 has a cylindrical round outer surface 404 that fits into a hollow cylindrical tube 406. The valve body 402 is sealed to the inside of the hollow cylindrical tube 406. In one embodiment, the hollow cylindrical tube 406 comprises a fitting to which passageways (such as passageways 120, 124) are fluidly connected. In another embodiment, the hollow cylindrical tube 406 is simply an insert in a continuous, unitary passageway that embraces two passageways (such as passageways 120, 124).

The valve 400 comprises first check valve 408 and second check valve 410. Check valves 408, 410 are formed in round, fluidly parallel passageways in the valve body 402. The check valves 408, 410 check (prevent) backflow of fluid through the check valves 408, 410. One of the check valves 408, 410 opens and permits forward fluid flow when a pressure differential across the valve exceeds a pressure differential threshold P. The pressure differential threshold P is substantially equal to a force F exerted by one of the springs 416, 418 multiplied by an open cross-sectional area of one of the port openings 420, 422. When a pressure differential between a bladder and a reservoir is below the pressure differential threshold P, then there is no flow through either check valve 408, 410. Under these low differential pressure conditions, if the bladder is inflated, it will remain inflated. If the bladder is deflated, it will remain deflated. Under normal use and storage conditions, both check valves are closed. When the patient applies an external compressive force to an inflated bladder, the threshold is exceeded in a first direction and the external force deflates the bladder. When the patient applies an external compressive force to the reservoir, the threshold is exceeded in a second, opposite direction and the external force on the reservoir inflates the bladder. The threshold P is controllable by the design of the check valves 408, 410, e.g. the size of spring and the open area of the valve seat. If desired, different thresholds P can be set for each valve to accommodate differences in external forces application areas between the bladder and reservoir. The valve 400 shown is exemplary, and other known types of valves can be used. In an alternative embodiment, the liquid in the system can be prepressurized and one check valve can be used that is manually actuatable to inflate the bladder.

An increased, selectable girth for a portion of the malleable penile prosthesis is provided. A relatively short section of the distal end of the column has an increase in girth. This is the portion of the cylinder that would initially, and perhaps primarily, be involved during intromission and as such would be the part of the cylinder most effective for its intended purpose. The girth increase is at the distal end of the prosthesis. Cross-sectional area is increased by transferring fluid from a small implanted reservoir to an expandable bladder. The reservoir can be alternately pressurized or non-pressurized. If the reservoir is pressurized, a valve, which is either opened by the patient or by the act of straightening the cylinder, lets the pressurized fluid pass through a transfer tube into the bladder. To deflate the bladder, the patient squeezes the penis over the bladder forcing the fluid back into the reservoir either via a check valve in the valve or by squeezing the valve. If the reservoir is non-pressurized, the fluid can be forced from the reservoir; the patient squeezes the perineal area and forces the fluid into the bladder. As with the pressurized reservoir design, to deflate the bladder the patient squeezes the penis over the bladder region. The squeezing forces the fluid back into the reservoir either via a one way check valve, or by squeezing the valve.

The embodiment shown in FIG. 2 provides an external reservoir that provides more fluid and increased volumetric expansion of the bladder. Large bladders that extend over a longer section of the column can be used with the embodiment shown in FIG. 2. If desired, the fluid can be pressurized at the time of manufacture, and the valve can be manually actuatable to inflate the bladder from the prepressurization.

Although the present invention has been described with reference to preferred embodiments, workers skilled in the art will recognize that changes may be made in form and detail without departing from the spirit and scope of the invention.

What is claimed is:

1. A penile prosthetic device, comprising:
    a malleable column formed of resilient material and having a proximal end and a distal end;
    a bladder having a liquid cavity at the distal end of the column, the bladder being inflatable and deflatable to increase and decrease a girth at the distal end of the prosthetic device, wherein the girth of the majority of the prosthetic device does not change responsive to the inflation or deflation of the bladder; and
    a liquid supply system for selectively controlling liquid flow to the bladder to increase and decrease the girth.

2. The prosthetic device of claim 1, wherein said liquid supply system is pressurized.

3. The prosthetic device of claim 1, wherein said liquid supply system is non-pressurized.

4. The prosthetic device of claim 2, wherein said liquid supply system includes a check valve.

5. The prosthetic device of claim 1, wherein the liquid supply system comprises:
    a reservoir for containing a liquid; and
    a passageway connecting the reservoir to the liquid cavity of the bladder;
    wherein at least a portion of the passageway is within the column.

6. The prosthetic device of claim 5, wherein the reservoir is within the column.

7. The prosthetic device of claim 1, wherein the bladder forms a ring around the column.

8. A penile prosthetic device, comprising:
    a malleable column formed of resilient material and having a length measured along a longitudinal axis of the column from a proximal end to a distal end;
    a bladder having a liquid cavity adjacent the distal end of the column and a length measured along the longitudinal axis that is less than half the length of the column, the bladder being inflatable and deflatable to increase and decrease a girth at the distal end of the prosthetic device; and
    a liquid supply system comprising:
        a reservoir for containing a liquid; and
        a passageway connecting the reservoir to the liquid cavity of the bladder, wherein at least a portion of the passageway is within the column.

9. The prosthetic device of claim 8, wherein a portion of the distal end of the column is not covered by the bladder.

10. The prosthetic device of claim 9, wherein the bladder forms a ring around the column.

11. The prosthetic device of claim 8, wherein the reservoir is within the column.

12. The prosthetic device of claim 8, wherein the reservoir is compressible.

13. The prosthetic device of claim 8, wherein said liquid supply system comprises a valve within the column.

14. A penile prosthetic device, comprising:
    a malleable column formed of resilient material and having a proximal end and a distal end;

a bladder having a liquid cavity forming a ring around the column at the distal end, the bladder being inflatable and deflatable to increase and decrease a girth at the distal end of the prosthetic device; and a liquid supply system comprising:
  a reservoir for containing a liquid; and
  a passageway connecting the reservoir to the liquid cavity of the bladder, wherein a portion of the passageway is within the column;
wherein the bladder is displaced from a location where the passageway enters the column.

15. The prosthetic device of claim 14, wherein a portion of the distal end of the column is not covered by the bladder.

16. The prosthetic device of claim 14, wherein said liquid supply system comprises a valve within the column.

17. The prosthetic device of claim 14, wherein the girth of the majority of the prosthetic device does not change responsive to the inflation or deflation of the bladder.

18. The prosthetic device of claim 14, wherein:
  the column has a length measured along a longitudinal axis of the column from a proximal end to a distal end; and
  the bladder has a length measured along the longitudinal axis that is less than half the length of the column.

* * * * *